United States Patent [19]

Lavielle et al.

[11] Patent Number: 5,296,494

[45] Date of Patent: Mar. 22, 1994

[54] PYRROLIDINE COMPOUNDS HAVING THROMBOXANE $A_2$ RECEPTOR ANTAGONISTIC ACTIVITY AND THROMBOXANE $A_2$ SYNTHASE INHIBITING ACTIVITY

[75] Inventors: Gilbert Lavielle, La Celle Saint Cloud; Patrick Hautefaye, Servon Brie Comte Robert; Michel Laubie, Vaucresson; Tony Verbeuren, Vernouillet, all of France

[73] Assignee: Adir et Compagnie, Courbevoie, France

[21] Appl. No.: 992,930

[22] Filed: Dec. 18, 1992

[30] Foreign Application Priority Data

Dec. 30, 1991 [FR] France .............................. 91 15851

[51] Int. Cl.$^5$ .................. A61K 31/44; C07D 401/06; C07D 207/48
[52] U.S. Cl. .................... 514/343; 514/333; 514/423; 514/424; 514/426; 514/428; 546/256; 546/281; 548/530; 548/531; 548/538; 548/539; 548/542; 548/557; 548/572
[58] Field of Search ............... 546/256, 281; 548/530, 548/531, 538, 539, 542, 572, 557; 514/333, 343, 423, 424, 426, 428

[56] References Cited

U.S. PATENT DOCUMENTS 4,916,152  4/1990  Setoi .................................... 548/413
5,168,101 12/1992  Arai ..................................... 548/538

OTHER PUBLICATIONS

Gallagher et al "Electrophile-mediated cyclization" J. Chem. Soc. Perk. Trans 1(4) 433–440 (1992).
Setoi et al "Preparation of 1-alkyl-2-(carboxyalkenyl-)-3-acylamino pyrrolidine as TBXA$_2$ antagonist" CA 114:42564q (1991).
Zeffren et al "The Study of Enzyme Mechanisms" John Wiley and Sons, p. 87 (1974).
Inhibition of Collagen-induced Human Platelet Activation in Citrated Whole Blood by ICI D1542, A Thromboxane A$_2$ Synthase Inhibitor and Cyclic Endoperoxide ... V. C. Menys, Platelets 3, 331–335 (1992).
Thromboxane Receptor Antagonism Combined with Thromboxane Synthase Inhibition 5. Synthesis and evaluation of Enantiomers of 8-[[(4–Cholorophenyl)-sulfonyl]amino ... S. S. Bhagwat et al., J. Med. Chem. 36, 205–210 (1993).
Ridogrel Inhibits Systemic and Renal Formation of Thromboxane A$_2$/Prostaglandin Endoperoxide Receptors upon Chronic Administration to Man, C. Weber et al., Thrombosis and Haemostasis 68(2), 214–220 (1992).
Bay u 3405, Thromboxane Endoperoxide Receptor Antagonist, Drugs of the Future 16(8): 701–705 (1991).
Antiplatelet Activity of the Long-Acting Thromboxane Receptor Antagonist BMS 180,291 in Monkeys, W. A. Schumacher et al., Prostaglandins 44, 389–397 (1992).

Primary Examiner—C. Warren Ivy
Assistant Examiner—Celia Chang
Attorney, Agent, or Firm—Gordon W. Hueschen

[57] ABSTRACT

Compounds of formula (I):

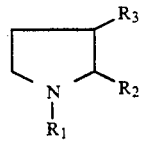

wherein $R_1$, $R_2$, $R_3$, m, n, and R are as defined in the Specification.

Medicinal products containing the same are useful in the treatment or prevention of thrombotic afflictions due to their thromboxane A$_2$ receptor antagonistic activity and their thromboxane A$_2$ synthase inhibitory activity.

7 Claims, No Drawings

PYRROLIDINE COMPOUNDS HAVING THROMBOXANE A₂ RECEPTOR ANTAGONISTIC ACTIVITY AND THROMBOXANE A₂ SYNTHASE INHIBITING ACTIVITY

The present invention relates to new pyrrolidine compounds.

More especially, the compounds described in the present invention possess antithromboxane $A_2$ properties, both as thromboxane $A_2$ ($TXA_2$) receptor antagonists, and as inhibitors of the activity of the enzyme responsible for thromboxane $A_2$ synthesis: thromboxane $A_2$ synthase.

Thromboxane $A_2$ is an arachidonic acid metabolite produced by blood platelets, which produces substantial constriction of blood vessels and induces platelet aggregation. Thromboxane $A_2$ production is increased in afflictions such as angina pectoris or stroke, and it plays a very important part in all processes leading to thrombotic afflictions.

It was hence especially advantageous to synthesize substances capable of inhibiting the aggregation- promoting and vasoconstrictor activities of thromboxane $A_2$, either as thromboxane $A_2$ receptor antagonists, or as thromboxane $A_2$ synthase inhibitors.

Pyrrolidine compounds possessing antithrombotic properties have been described in the literature. This applies, in particular, to the compounds described in Patents EP 289,911 and EP 367,130.

The compounds described in the present invention, apart from the fact that they are new, possess pharmacological properties markedly more intense than those of the other compounds described in the prior art.

They are hence useful as thromboxane $A_2$ antagonists and as thromboxane $A_2$ synthase inhibitors in the treatment or prevention of thrombotic afflictions such as stroke, angina pectoris, myocardial infarction, peripheral circulatory insufficiency, afflictions linked to thrombus formation, etc.

More specifically, the present invention relates to the compounds of formula (I):

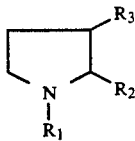

(I)

in which:

$R_1$ represents:
- a linear or branched ($C_1$-$C_6$) alkyl group, unsubstituted or substituted with a 2-pyridyl, 3-pyridyl or phenyl (itself optionally substituted with one or more halogen atoms or linear or branched ($C_1$-$C_6$) alkyl, linear or branched ($C_1$-$C_6$) alkoxy or trihalomethyl groups) group,
- a phenyl group, unsubstituted or substituted with one or more hydrogen atoms or linear or branched ($C_1$-$C_6$) alkyl, linear or branched ($C_1$-$C_6$) alkoxy or trihalomethyl groups,
- a pyridyl group,
- a phenylsulfonyl group, unsubstituted or substituted on the phenyl ring with one or more halogen atoms or linear or branched ($C_1$-$C_6$) alkyl, linear or branched ($C_1$-$C_6$) alkoxy or trihalomethyl groups,
- a linear or branched ($C_1$-$C_6$) acyl group,
- a linear or branched ($C_1$-$C_6$) alkoxycarbonyl group,
- a benzoyl (unsubstituted or substituted on the phenyl ring with one or more halogen atoms or hydroxyl, alkyl, alkoxy or trifluoromethyl groups) or pyridylcarbonyl group,
- an alkylaminocarbonyl or phenylaminocarbonyl (unsubstituted or substituted on the phenyl ring with one or more halogen atoms or hydroxyl, alkyl, alkoxy or trifluoromethyl groups) group,
- an acylamino or benzoylamino group, $R_2$ represents:
- a phenyl group, unsubstituted or substituted with one or more halogen atoms or linear or branched ($C_1$-$C_6$) alkyl, linear or branched ($C_1$-$C_6$) alkoxy, hydroxyl or trihalomethyl groups,
- a 3-pyridyl or 2-pyridyl group, $R_3$ represents any one of the following groups:

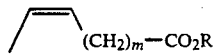

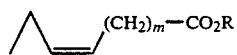

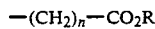

in which
m is equal to 2, 3 or 4,
n is equal to 4, 5, 6 or 7,
and R represents a hydrogen atom or a linear or branched ($C_1$-$C_6$) alkyl group, their enantiomers, diastereoisomers and epimers as well as their addition salts with a pharmaceutically acceptable acid or base.

Among pharmaceutically acceptable acids, there may be mentioned, without implied limitation, hydrochloric, sulfuric, tartaric, maleic, fumaric, methanesulfonic and camphoric acids, and the like.

Among pharmaceutically acceptable bases, there may be mentioned, without implied limitation, sodium hydroxide, potassium hydroxide, tert-butylamine, diethylamine, ethylenediamine, and the like.

The invention also extends to the process for preparing the compounds of formula (I), wherein a pyrrolidine of formula (II):

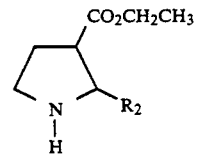

(II)

in which $R_2$ has the same meaning as in the formula (I), in racemic form or the isomers of which compound have been separated beforehand according to a standard separation technique, is used as starting material, which compound is reacted:

either with lithium aluminum hydride in ether, to yield the pyrrolidine of formula (III):

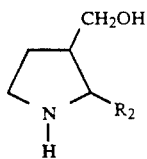 (III)

in which $R_2$ has the same meaning as in the formula (I), which is then reacted with a halogenated compound of formula $R_1X$, in which $R_1$ has the same meaning as in the formula (I) and X represents a halogen atom, in chloroform in the presence of triethylamine or in acetonitrile in the presence of potassium carbonate, to yield the pyrrolidine of formula (IV):

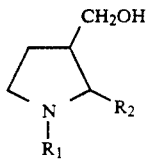 (IV)

in which $R_1$ and $R_2$ have the same meaning as in the formula (I),
or with a halogenated compound of formula $R_1X$ as defined above,
to yield the pyrrolidine of formula (V):

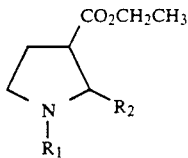 (V)

in which $R_1$ and $R_2$ have the same meaning as in the formula (I), which compound of formula (V), when it is in the form of a pair of enantiomers, may be converted, if so desired, to its other pair of enantiomers by the reaction of sodium ethanolate in an ethanolic medium, which compound of formula (V) is reduced:
a either:
in the presence of two equivalents of diisobutylaluminum hydride in toluene, to yield the pyrrolidine of formula (IV) defined above, which compound of formula (IV), irrespective of the synthesis route by which it has been obtained, is converted to the corresponding tosylate (Ts) of formula (VI) by reaction with toluenesulfonyl chloride in the presence of pyridine,

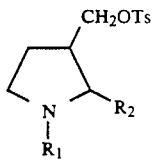 (VI)

in which $R_1$ and $R_2$ have the same meaning as in the formula (I), which is reacted with potassium cyanide in a dimethyl sulfoxide medium, to yield the pyrrolidine of formula (VII):

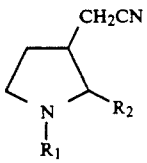 (VII)

in which $R_1$ and $R_2$ have the same meaning as in the formula (I), which is reduced by means of diisobutylaluminum hydride in toluene, to yield the corresponding aldehyde of formula (VIII):

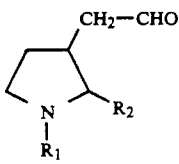 (VIII)

in which $R_1$ and $R_2$ have the same meaning as in the formula (I),
b or:
in the presence of one equivalent of diisobutylaluminum hydride in toluene, to yield the pyrrolidine of formula (IX):

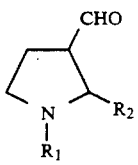 (IX)

in which $R_1$ and $R_2$ have the same meaning as in the formula (I), which compounds of formula (VIII) or (IX) are reacted with a phosphorus ylide of formula (X), prepared by reaction of the corresponding phosphonium salt, in the presence of potassium tert-butanolate in tetrahydrofuran, $$(C_6H_5)_3 P=CH-(CH_2)_m-CO_2H \quad (X)$$

in which m has the same meaning as in the formula (I), to yield, respectively, the compounds of formula (I/a) or (I/b), a special case of the compounds of formula (I):

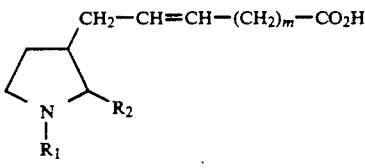 (I/a)

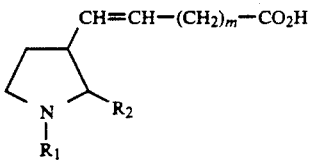 (I/b)

in which $R_1$, $R_2$ and m have the same meaning as in the formula (I), which compounds of formula (I/a) or (I/b) are esterified, if so desired, to yield the corresponding compounds of formula (I/a$_1$) and (I/b$_1$):

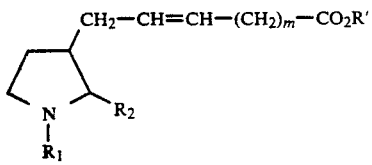

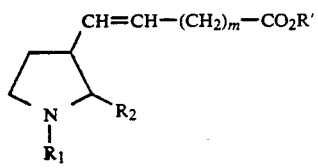

in which $R_1$ and $R_2$ have the same meaning as in the formula (I) and R' represents a linear or branched ($C_1$-$C_6$) alkyl group, the double bond of which is optionally reduced by catalytic hydrogenation to yield the compound of formula (I/c), a special case of the compounds of formula (I),

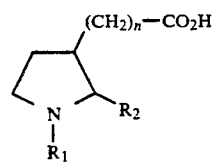

in which $R_1$, $R_2$ and n have the same meaning as in the formula (I), and which is converted, if so desired, to the corresponding ester of formula (I/c$_1$):

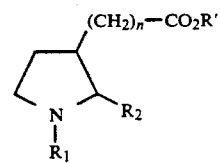

in which $R_1$ and $R_2$ have the same meaning as in the formula (I) and R' represents a linear or branched ($C_1$-$C_6$) alkyl group, which compounds of formula (I/a), (I/a$_1$), (I/b), (I/b$_1$), (I/c) and (I/c$_1$) constitute the set of compounds of formula (I), which, when $R_2$ represents a phenyl ring substituted with a linear or branched ($C_1$-$C_6$) alkoxy group, may be converted, if so desired, to compounds of formula (I) in which $R_2$ represents a phenyl ring substituted with a hydroxyl group, which are purified, where appropriate, according to a standard purification technique, the isomers of which are optionally separated according to a standard separation technique, and which are converted, if so desired, to their addition salts with a pharmaceutically acceptable acid or base.

The compounds of formula (I) possess very advantageous pharmacological properties. In particular, they are capable of inhibiting platelet aggregation induced by U46619 (9,11-dideoxy-11α,9α-epoxymethanoprostaglandin $F_{2\alpha}$), a TXA$_2$ receptor agonist, of inhibiting contractions caused by U46619 on guinea pig trachea and of preventing in vivo U46619-induced bronchoconstrictions in guinea pigs. In addition, the compounds inhibit TXA$_2$ synthesis in the blood of rabbit.

The subject of the present invention is also pharmaceutical compositions containing as active principle at least one compound of formula (I), alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, hard gelatin capsules, troches, suppositories, creams, ointments, skin gels, and the like.

The appropriate dosage varies according to the patient's age and weight, the nature and severity of the complaint and also the administration route. The latter can be oral, nasal, rectal or parenteral. Generally speaking, the unit dosage ranges between 10 and 200 mg for a treatment administered in 1 to 3 doses per 24 hours.

The examples which follow illustrate the invention and in no way limit it.

The starting materials used are known products or products prepared according to known procedures.

The letters α and β mean that the hydrogens of the pyrrolidine are in the cis position with respect to one another in the case of (2α,3α) and in the trans position with respect to one another in the case of (2α,3β).

EXAMPLE 1

(4Z)-6-[(2α,3α)-1-(4-Fluorophenylsulfonyl)-2-(3-methoxyphenyl)-3-pyrrolidinyl]-4- hexenoic acid sodium salt

STAGE A:

Ethyl (2α,3α)-1-(4-fluorophenylsulfonyl)-2-(3-methoxyphenyl)-3-pyrrolidinecarboxylate A solution containing 85.2 mmol of 4-fluorobenzenesulfonyl chloride in 100 ml of chloroform is added in small portions to a stirred solution at room temperature containing 77.4 mmol of ethyl (2α,3α)-2-(3- methoxyphenyl)-3-pyrrolidinecarboxylate (prepared according to the procedure described in Can. J. Chem., 60 (7), 926, 1982) and 92.9 mmol of triethylamine in 300 ml of chloroform. Stirring is maintained for three hours. After washing of the chloroform phase with water, drying and evaporation of the solvent, the expected product is obtained by filtering off the residue on silica with dichloromethane.

Yield: 93%

Proton nuclear magnetic resonance (CDCl$_3$/TMS):

The coupling constant J between the two geminal protons 2α and 3α of the pyrrolidine is equal to 8 Hz.

STAGE B:

(2α,3α)-1-(4-Fluorophenylsulfonyl)-2-(3-methoxyphenyl)-3-(hydroxymethyl) pyrrolidine A 1.5M solution containing 66.2 mmol of diisobutylaluminum hydride in toluene is added in small portions to a stirred solution at −50° C., under an inert atmosphere, containing 33.1 mmol of the compound obtained in the preceding stage in 250 ml of toluene. Stirring is maintained for 30 minutes while the mixture is allowed to return to room temperature. The reaction medium is then hydrolyzed using 50% sodium bisulfite solution. The expected product is obtained after filtration, drying and evaporation of the filtrate, and crystallizes slowly.

Yield: 80%

Melting point: 71° C.
Proton nuclear magnetic resonance (CDCl3/TMS):
The coupling constant J between the two geminal protons 2α and 3α of the pyrrolidine is equal to 8 Hz.

STAGE C:

(2α,3α)-1-(4-Fluorophenylsulfonyl)-2-(3-methoxyphenyl)-3-(cyanomethyl) pyrrolidine A solution containing 31.7 mmol of the compound obtained in the preceding stage and 36.8 mmol of tosyl chloride in 175 ml of pyridine is stirred for 48 hours at room temperature. The reaction medium is then hydrolyzed on 400 g of ice and extracted several times with dichloromethane. The organic phases are dried and evaporated and yield the corresponding tosylate, which is heated to 100° C. for 18 hours in 130 ml of dimethyl sulfoxide in the presence of 27 mmol of potassium cyanide. After cooling and hydrolysis of the medium on 400 g of ice, the expected product precipitates and is filtered off, washed with diisopropyl ether and dried.
Yield: 60%
Melting point: 134° C.
Proton nuclear magnetic resonance (CDCl3/TMS):
The coupling constant J between the two geminal protons 2α and 3α of the pyrrolidine is equal to 7.5 Hz.

STAGE D:

[(2α,3α)-1-(4-Fluorophenylsulfonyl)-2-(3-methoxyphenyl)-3-pyrrolidinyl]acetaldehyde A 1.5M solution containing 21.4 mmol of diisobutylaluminum hydride in toluene is added in small portions to a stirred suspension, under an inert atmosphere, at −60° C., containing 21.4 mmol of the compound obtained in the preceding stage in 300 ml of toluene. The mixture is stirred at −60° C. and then for 2 hours at −10° C. The reaction medium is then hydrolyzed at −10° C. with 100 ml of a methanol/water (50:50) solution. After filtration, the filtrate is extracted with dichloromethane. The organic phases are then dried and evaporated, and the expected product is obtained after purification of the residue by chromatography on silica gel, using a toluene/methanol (95:5) mixture as elution solvent.
Yield: 60%
Proton nuclear magnetic resonance (CDCl3/TMS):
The coupling constant J between the two geminal protons 2α and 3α of the pyrrolidine is equal to 7.5 Hz.

STAGE E:

(4Z)-6-[(2α,3α)-1-(4-Fluorophenylsulfonyl)-2-(3-methoxyphenyl)-3-pyrrolidinyl]-4- hexenoic acid 21.2 ml of a 1N solution of potassium tert- butylate in tetrahydrofuran are added slowly to a stirred suspension at room temperature, under an inert atmosphere, containing 10.6 mmol of 4-(triphenylphosphonio)- butanoic acid chloride in 40 ml of anhydrous tetrahydrofuran. The medium is stirred for one hour at room temperature and then cooled to 0° C. before the dropwise addition of 5.3 mmol of the compound obtained in the preceding stage dissolved in 5 ml of tetrahydrofuran. The reaction is monitored by thin-layer chromatography. The reaction medium is then hydrolyzed with 10 ml of saturated ammonium chloride solution. After filtration, the filtrate is washed with ether. The aqueous phase is acidified with hydrochloric acid and extracted with dichloromethane. The organic phases are washed with water, dried and evaporated. The expected product is obtained in acid form after purification of the residue by chromatography on silica gel, using a chloroform/ methanol (97:3) mixture as elution solvent.
Yield: 50%
Proton nuclear magnetic resonance (CDCl3/TMS):
The coupling constant J between the two geminal protons 2α and 3α of the pyrrolidine is equal to 7.5 Hz.

The acid is then converted to the corresponding sodium salt by addition of 1N sodium hydroxide to a methanolic solution of the acid, stirring for one hour at room temperature, evaporation and precipitation of the salt using ether.

| | Elemental microanalysis (sodium salt): | | | |
|---|---|---|---|---|
| | C % | H % | N % | S % |
| Calculated | 58.84 | 5.37 | 2.98 | 6.83 |
| Found | 59.09 | 5.39 | 3.03 | 6.61 |

Examples 2 to 6 were obtained according to the same procedure as that described for Example 1, using the appropriate starting materials.

EXAMPLE 2

(4Z)-6-[(2α,3α)-1-(4-Fluorophenylsulfonyl)-2-(3-pyridyl)-3-pyrrolidinyl]-4-hexenoic acid sodium salt Yield (stage E): 40%
Proton nuclear magnetic resonance (DMSO-d6/TMS):
The coupling constant J between the two geminal protons 2α and 3α of the pyrrolidine is equal to 7.5 Hz.

| | Elemental microanalysis: | | | |
|---|---|---|---|---|
| | C % | H % | N % | S % |
| Calculated | 57.26 | 5.03 | 6.36 | 7.28 |
| Found | 57.52 | 5.23 | 6.35 | 7.53 |

EXAMPLE 3

(4Z)-6-[(2α,3α)-1-(4-Fluorophenylsulfonyl)-2-(4-chlorophenyl)-3-pyrrolidinyl]-4-hexenoic acid sodium salt Yield (stage E): 62%
Proton nuclear magnetic resonance (CDCl3/TMS):
The coupling constant J between the two geminal protons 2α and 3α of the pyrrolidine is equal to 7.5 Hz.
Mass spectrum: Electron impact
M+: m/z=451 (theory: 451.9)

EXAMPLE 4

(4Z)-6-[(2α,3α)-1-(4-Fluorophenylsulfonyl)-2-phenyl-3-pyrrolidinyl]-4-hexenoic acid sodium salt Yield (stage E): 45%
Proton nuclear magnetic resonance (CDCl3/TMS):
The coupling constant J between the two geminal protons 2α and 3α of the pyrrolidine is equal to 8 Hz.

| | Elemental microanalysis: | | | | |
|---|---|---|---|---|---|
| | C % | H % | N % | Cl % | S % |
| Calculated | 57.96 | 5.08 | 3.07 | 7.78 | 7.03 |
| Found | 57.64 | 5.21 | 3.07 | 7.54 | 6.93 |

EXAMPLE 5

(4Z)-6-[(2α,3α)-1-Benzyl-2-(3-pyridyl)-3-pyrrolidinyl]-4-hexenoic acid sodium salt Yield (stage E): 30%
Proton nuclear magnetic resonance (CDCl$_3$/TMS):
The coupling constant J between the two geminal protons 2α and 3α of the pyrrolidine is equal to 7.5 Hz.

| | Elemental microanalysis: | | |
|---|---|---|---|
| | C % | H % | N % |
| Calculated | 75.28 | 7.40 | 7.81 |
| Found | 75.40 | 7.48 | 7.99 |

EXAMPLE 6

(5Z)-7-[(2α,3α)-1-(4-Fluorophenylsulfonyl)-2-(3-methoxyphenyl)-3-pyrrolidinyl]-5-heptenoic acid sodium salt Yield (stage E): 50%
Proton nuclear magnetic resonance (CDCl$_3$/TMS):
The coupling constant J between the two geminal protons 2α and 3α of the pyrrolidine is equal to 7.5 Hz.

EXAMPLE 7

(4Z)-6-{(2α,3α)-1-[(2-Pyridyl)methyl]-2-phenyl-3-pyrrolidinyl}-4-hexenoic acid sodium salt

STAGE A:
(2α,3α)-2-Phenyl-3-(hydroxymethyl)pyrrolidine

A solution containing 68.4 mmol of ethyl (2α,3α)-2-phenyl-3-pyrrolidinecarboxylate (prepared according to the procedure described in Can. J. Chem., 60 (7), 926, 1982) in 100 ml of ether is added dropwise to a suspension at 0° C. of 68.4 mmol of lithium aluminum hydride in 100 ml of ether. The reaction medium is kept stirring for 30 minutes at 0° C. 15 ml of ethyl acetate and 20 ml of saturated aqueous ammonium chloride solution are then added. After filtration of the precipitate formed, the filtrate is washed with water and the expected product is obtained after drying and evaporation of the aqueous phase.
Yield: 92%
Proton nuclear magnetic resonance (CDCl$_3$/TMS):
The coupling constant J between the two geminal protons 2α and 3α of the pyrrolidine is equal to 7.3 Hz.

STAGE B:
(2α,3α)-1-[(2-Pyridyl)methyl]-2-phenyl-3-(hydroxymethyl)pyrrolidine The expected product is obtained using the procedure described in stage A of Example 1, but replacing 4-fluorobenzenesulfonyl chloride by 2-(chloromethyl)pyridine.
Yield: 87%
Proton nuclear magnetic resonance (CDCl$_3$/TMS):
The coupling constant J between the two geminal protons 2α and 3α of the pyrrolidine is equal to 6 Hz.

STAGES C to E

Stages C to E of this example are identical to stages C to E of Example 1.

Stage E

Yield: 35%

Proton nuclear magnetic resonance (CDCl$_3$/TMS):
The coupling constant J between the two geminal protons 2α and 3α of the pyrrolidine is equal to 8 Hz.

| | Elemental microanalysis: | | |
|---|---|---|---|
| | C % | H % | N % |
| Calculated | 70.95 | 6.77 | 7.52 |
| Found | 71.07 | 6.98 | 7.47 |

EXAMPLE 8

(4Z)-6-[(2α,3α)-1-Nicotinoyl-2-phenyl-3-pyrrolidinyl]-4-hexenoic acid sodium salt This compound is synthesized using the same procedure as that described in Example 7, using the corresponding starting materials.

EXAMPLE 9

(4Z)-6-[(2α,3β)-1-(4-Fluorophenylsulfonyl)-2-(3-methoxyphenyl)-3-pyrrolidinyl]-4-hexenoic acid sodium salt

STAGE A: Ethyl (2α,3α)-1-(4-fluorophenylsulfonyl)-2-(3-methoxyphenyl)-3-pyrrolidinecarboxylate This stage is identical to stage A of Example 1.

STAGE A': Ethyl (2α,3β)-1-(4-fluorophenylsulfonyl)-2-(3-methoxyphenyl)-3-pyrrolidinecarboxylate The expected product is obtained by epimerization of the compound described in the preceding stage, by stirring 40 mmol of this compound in 30 ml of ethanol in the presence of 40 mmol of sodium ethylate at room temperature for 2 hours. After evaporation of the solvent, the residue is hydrolyzed with 5 ml of water and extracted with dichloromethane. The expected product is obtained after drying and evaporation of the organic phases.
Yield: 90%
Proton nuclear magnetic resonance (CDCl$_3$/TMS):
The coupling constant J between the two geminal protons 2α and 3β of the pyrrolidine is equal to 4.5 Hz.

STAGES B to E

These stages are identical to those described in Example 1.
Yield (stage E): 38%
Proton nuclear magnetic resonance (CDCl$_3$/TMS):
The coupling constant J between the two geminal protons 2α and 3β of the pyrrolidine is equal to 11 Hz.

Examples 10 and 11 were synthesized according to the same process as that described in Example 9, using the corresponding starting materials.

EXAMPLE 10

(4Z)-6-[(2α,3β)-1-Benzyl-2-(3-methoxyphenyl)-3-pyrrolidinyl]-4-hexenoic acid hydrochloride Yield (stage E): 53%
Proton nuclear magnetic resonance (CDCl$_3$/TMS):
The coupling constant J between the two geminal protons 2α and 3β of the pyrrolidine is equal to 11 Hz.
Mass spectrum (acid): Electron impact
M$^+$: m/z=379 (theory: 379.5)

EXAMPLE 11

(5Z)-7-[(2α,3β)-1-Benzyl-2-(3-methoxyphenyl)-3-pyrrolidinyl]-5-heptenoic acid hydrochloride Yield (stage E): 38%
Proton nuclear magnetic resonance (CDCl₃/TMS):
The coupling constant J between the two geminal protons 2α and 3β of the pyrrolidine is equal to 11 Hz.

EXAMPLE 12

(4Z)-5-[(2α,3α)-1-(4-Chlorophenylsulfonyl)-2-phenyl-3-pyrrolidinyl]-4-pentenoic acid sodium salt STAGE A: Ethyl (2α,3α)-1-(4-chlorophenylsulfonyl)-2-phenyl-3-pyrrolidinecarboxylate The expected product is obtained using the procedure described in stage A of Example 1, using the corresponding starting material.

STAGE B: [(2α,3α)-1-(4-Chlorophenylsulfonyl)-2-phenyl-3-pyrrolidinyl]acetaldehyde The expected product is obtained using the procedure described in stage D of Example 1, using the product described in the preceding stage.

STAGE C:
(4Z)-5-[(2α,3α)-1-(4-Chlorophenylsulfonyl)-2-phenyl-3-pyrrolidinyl]-4-pentenoic acid sodium salt The expected product is obtained using the procedure described in stage E of Example 1, using the product described in the preceding stage.

Yield: 20%
Proton nuclear magnetic resonance (CDCl₃/TMS):
The coupling constant J between the two geminal protons 2α and 3α of the pyrrolidine is equal to 7 Hz.

EXAMPLE 13

(5Z)-6-[(2α,3α)-1-(4-Fluorophenylsulfonyl)-2-(4-chlorophenyl)-3-pyrrolidinyl]-5-hexenoic acid This compound is obtained according to the same process as that described in Example 12, using the corresponding starting materials.

Yield (stage E): 20%
Proton nuclear magnetic resonance (CDCl₃/TMS):
The coupling constant J between the two geminal protons 2α and 3α of the pyrrolidine is equal to 7.5 Hz.

EXAMPLE 14

(4Z)-6-[(2α,3α)-1-(4-Fluorophenylsulfonyl)-2-(3-hydroxyphenyl)-3-pyrrolidinyl]-4-hexenoic acid sodium salt 0.84 ml of an 8M solution of boron tribromide in dichloromethane is added dropwise to a stirred solution at −78° C. containing 11 mmol of the compound described in Example 1 in 50 ml of dichloromethane. The reaction medium is kept stirring for 4 hours after it has returned to room temperature. It is then hydrolyzed with 10 ml of saturated ammonium chloride solution and 10 ml of methanol. After extraction with dichloromethane, the organic phases are dried and evaporated. The expected product is obtained after purification of the residue by chromatography on silica gel, using a dichloromethane/ methanol (95:5) mixture as elution solvent, and converted to the corresponding sodium salt.

Yield: 94%

Proton nuclear magnetic resonance (DMSO-d₆/TMS):
The coupling constant J between the two geminal protons 2α and 3α of the pyrrolidine is equal to 7.5 Hz.

| | Elemental microanalysis: | | | |
|---|---|---|---|---|
| | C % | H % | N % | S % |
| Calculated | 58.01 | 5.09 | 3.08 | 7.07 |
| Found | 57.99 | 5.41 | 2.97 | 6.89 |

Examples 15, 16 and 17 were prepared according to the same process as that described in Example 14, using the appropriate starting materials.

EXAMPLE 15

(5Z)-7-[(2α,3α)-1-(4-Fluorophenylsulfonyl)-2-(3-hydroxyphenyl)-3-pyrrolidinyl]-5-heptenoic acid sodium salt Yield: 75%
Proton nuclear magnetic resonance (DMSO-d₆/TMS):
The coupling constant J between the two geminal protons 2α and 3α of the pyrrolidine is equal to 7.5 Hz.

| | Elemental microanalysis: | | | |
|---|---|---|---|---|
| | C % | H % | N % | S % |
| Calculated | 58.84 | 5.37 | 2.98 | 6.83 |
| Found | 58.47 | 5.49 | 3.03 | 6.94 |

EXAMPLE 16

(4Z)-6-[(2α,3β)-1-Benzyl-2-(3-hydroxyphenyl)-3-pyrrolidinyl]-4-hexenoic acid hydrobromide Yield: 80%
Proton nuclear magnetic resonance (DMSO-d₆/TMS):
The coupling constant J between the two geminal protons 2α and 2β of the pyrrolidine is equal to 10 Hz.

| | Elemental microanalysis: | | | |
|---|---|---|---|---|
| | C % | H % | N % | S % |
| Calculated | 61.89 | 6.32 | 3.14 | 17.90 |
| Found | 61.83 | 6.40 | 3.02 | 17.60 |

EXAMPLE 17

(4Z)-6-[(2α,3β)-1-(4-Fluorophenylsulfonyl)-2-(3-hydroxyphenyl)-3-pyrrolidinyl]-4-hexenoic acid sodium salt Yield: 74%
Proton nuclear magnetic resonance (acid) (CDCl₃/TMS):
The coupling constant J between the two geminal protons 2α and 3β of the pyrrolidine is equal to 11 Hz.

| | Elemental microanalysis: | | | |
|---|---|---|---|---|
| | C % | H % | N % | S % |
| Calculated | 58.01 | 5.09 | 3.08 | 7.04 |

-continued

| | Elemental microanalysis: | | | |
|---|---|---|---|---|
| | C % | H % | N % | S % |
| Found | 57.91 | 5.39 | 3.09 | 6.87 |

EXAMPLE 18

7-[(2α,3α)-1-(4-Fluorophenylsulfonyl)-2-(3-hydroxyphenyl)-3-pyrrolidinyl]heptanoic acid sodium salt A solution containing 1.06 mmol of the compound described in Example 15, in 25 ml of ethanol, is stirred at room temperature and atmospheric pressure under a hydrogen atmosphere in the presence of 50 mg of palladium on charcoal (10% Pd). After filtration of the catalyst, the expected product is obtained by evaporation of the solvent and crystallization in ether.

Yield: 99%
Melting point: 180°-182° C.
Proton nuclear magnetic resonance (CDCl₃/TMS):
The coupling constant J between the two geminal protons 2α and 3α of the pyrrolidine is equal to to 7 Hz.

| | Elemental microanalysis: | | | |
|---|---|---|---|---|
| | C % | H % | N % | S % |
| Calculated | 58.59 | 5.77 | 2.97 | 6.80 |
| Found | 57.92 | 5.83 | 3.03 | 6.47 |

Examples 19 and 20 were prepared according to the same procedure as that described in Example 18, using the appropriate starting materials.

EXAMPLE 19

6-[(2α,3α)-1-Phenylsulfonyl-2-phenyl-3-pyrrolidinyl]-hexanoic acid sodium salt

Yield: 99%
Melting point: 170°-174° C.
Proton nuclear magnetic resonance (CDCl₃/TMS):
The coupling constant J between the two geminal protons 2α and 3α of the pyrrolidine is equal to 7.5 Hz.

| | Elemental microanalysis: | | | |
|---|---|---|---|---|
| | C % | H % | N % | S % |
| Calculated | 62.39 | 6.19 | 3.31 | 7.57 |
| Found | 62.21 | 6.21 | 3.41 | 6.79 |

EXAMPLE 20

6-[(2α,3α)-1-(4-Fluorophenylsulfonyl)-2-(3-pyridyl)-3-pyrrolidinyl) hexanoic acid sodium salt Yield: 99%
Proton nuclear magnetic resonance (CDCl₃/TMS):
The coupling constant J between the two geminal protons 2α and 3α of the pyrrolidine is equal to 7.5 Hz.

| | Elemental microanalysis: | | | |
|---|---|---|---|---|
| | C % | H % | N % | S % |
| Calculated | 57.00 | 5.47 | 6.33 | 7.25 |
| Found | 56.92 | 5.55 | 6.20 | 6.81 |

EXAMPLE 21

(4Z)-6-((2α,3α)-1-[(3-Pyridyl)methyl]-2-phenyl-3-pyrrolidinyl]-4-hexenoic acid sodium salt STAGE A: Ethyl (2α,3α)-1-[(3-pyridyl)methyl]-2-phenyl-3-pyrrolidinecarboxylate A solution of 75.2 mmol of 3-(chloromethyl)pyridine in 50 ml of acetonitrile is added in small portions to a stirred suspension at room temperature containing 68.4 mmol of ethyl (2α,3α)-2-phenyl-3-pyrrolidinecarboxylate (prepared according to the procedure described in Can. J. Chem. 60, (7), 926, 1982) and 167 mmol of potassium carbonate in 200 ml of acetonitrile. Stirring is maintained for 48 hours. After filtration of the salts and concentration of the solvent, the product is obtained by chromatography on silica gel, using a dichloromethane/methanol (95:5) mixture as eluent.

Yield: 93%
Proton nuclear magnetic resonance (CDCl₃/TMS):
The coupling constant J between the two geminal protons 2α and 3α of the pyrrolidine is equal to 8 Hz.

STAGE B: (2α,3α)-1-[(3-Pyridyl)methyl]-2-phenyl-3-(hydroxymethyl)pyrrolidine

The expected product is obtained using the procedure described in stage A of Example 7, but replacing ether by tetrahydrofuran.

Yield: 66%
Melting point: 139° C.
Proton nuclear magnetic resonance (CDCl₃/TMS):
The coupling constant J between the two geminal protons 2α and 3α of the pyrrolidine is equal to 7 Hz.

STAGES C AND D

Identical to stages C and D of Example 1.

STAGE E: Methyl (2α,3α)-{1-[(3-pyridyl)methyl]-2-phenyl-3-pyrrolidinyl}-4-hexenoate 21.2 ml of a 1N solution of potassium tert-butylate in tetrahydrofuran is added slowly to a stirred suspension at room temperature, under an inert atmosphere, containing 10.6 mmol of 4-(triphenylphosphonio)butanoic acid chloride in 40 ml of anhydrous tetrahydrofuran. The medium is stirred for one hour at room temperature and then cooled to 0° C. before the dropwise addition of 5.3 mmol of the compound obtained in the preceding stage dissolved in 5 ml of tetrahydrofuran. The reaction medium is stirred for 2 hours at room temperature and then hydrolyzed with 10 ml of saturated ammonium chloride solution. After filtration, the filtrate is washed with ether. The aqueous phase is brought back to pH 7 by adding acetic acid, and then extracted with dichloromethane. The organic phase is cooled to 0° C., and a solution of diazomethane in ether is added dropwise until the yellow coloration persists. The excess diazomethane is destroyed by adding one drop of acetic acid. The reaction medium is dried over magnesium sulfate and the solvent is evaporated off. The expected product is obtained after purification of the residue by chromatography on silica gel, using a dichloromethane/methanol mixture as eluent.

Yield: 93%
Proton nuclear magnetic resonance (CDCl₃/TMS):
The coupling constant J between the two geminal protons 2α and 3α of the pyrrolidine is equal to 8 Hz.

STAGE F:
(4Z)-6-{(2α,3α)-1-[(3-Pyridyl)methyl]-2-phenyl-3-pyrrolidinyl}-4-hexenoic acid sodium salt The product obtained in the preceding stage, dissolved in 50 ml of methanol, is saponified by adding 35 ml of 1N sodium hydroxide. After refluxing for 2 hours, the medium is concentrated to one half and the expected product is extracted with dichloromethane.

Yield: 46%

Proton nuclear magnetic resonance (CDCl$_3$/TMS):

The coupling constant J between the two geminal protons 2α and 3α of the pyrrolidine is equal to 7 Hz.

| | Elemental microanalysis: | | |
|---|---|---|---|
| | C % | H % | N % |
| Calculated | 70.95 | 6.77 | 7.52 |
| Found | 71.07 | 7.05 | 7.47 |

EXAMPLE 22
6-{(2α,3α)-1-[(3-Pyridyl)methyl]-2-phenyl-3-pyrrolidinyl}hexanoic acid sodium salt STAGE A: Methyl 6-{(2α,3α)-1-[(3-pyridyl)methyl]-2-phenyl-3-pyrrolidinyl}hexanoate This compound is prepared from the compound described in stage E of Example 21, according to the same procedure as that described in Example 18.

Yield: 99%

Proton nuclear magnetic resonance (CDCl$_3$/TMS):

The coupling constant J between the two geminal protons 2α and 3α of the pyrrolidine is equal to 8 Hz.

STAGE B: 6-{(2α,3α)-1-[(3-Pyridyl)methyl]-2-phenyl-3-pyrrolidinyl}hexanoic acid sodium salt Identical to stage F of Example 21.
Yield: 57%
Melting point: 164° C.

| | Elemental microanalysis: | | |
|---|---|---|---|
| | C % | H % | N % |
| Calculated | 70.57 | 7.27 | 7.48 |
| Found | 69.69 | 7.12 | 7.44 |

EXAMPLE 23
(4Z)-[(2α,3α)-1-tert-Butoxycarbonyl-2-(3-pyridyl)-3-pyrrolidinyl]-4-hexenoic acid sodium salt STAGE A: (2α,3α)-tert-Butoxycarbonyl-2-(3-pyridyl)-3-(hydroxymethyl)pyrrolidine A solution containing 0.404 mol of ethyl (2α,3α)-2-(3-pyridyl)-3-pyrrolidinecarboxylate (prepared according to Can. J. Chem. 60, (7), 926, 1982) in 1 l of ether is added dropwise to a suspension at 0° C. of 0.808 mol of lithium aluminum hydride in 500 ml of ether. The reaction medium is kept stirring for 1 hour at 0° C. 50 ml of ethyl acetate are then added, followed by 200 ml of water. After filtration of the precipitate formed and taking up with 0.1N sodium hydroxide, the ether is evaporated off, and the resulting aqueous phase is cooled to 0° C. after adding 200 ml of dioxane. A solution containing 0.412 mol of tert-butylcarbonate in 200 ml of dioxane is added. The reaction medium is stirred for one hour at room temperature and extracted with dichloromethane. After evaporation of the solvents, the expected product is crystallized in an isopropyl ether/pentane (50:50) mixture.

Yield: 69%
Melting point: 90.5° C.

STAGES B to E

Stages B to E of this example are identical to stages C to F of Example 21.

STAGE F:
(4Z)-[(2α,3α)-1-tert-Butoxycarbonyl-2-(3-pyridyl)-3-pyrrolidinyl]-4-hexenoic acid sodium salt Yield: 51%

| | Elemental microanalysis: | | |
|---|---|---|---|
| | C % | H % | N % |
| Calculated | 62.81 | 7.12 | 7.32 |
| Found | 61.90 | 6.95 | 7.13 |

EXAMPLE 24
(4Z)-6-[(2α,3α)-1-(4-Chlorophenylaminocarbonyl)-2-(3-pyridyl)-3-pyrrolidinyl]-4-hexenoic acid sodium salt STAGE A: Methyl (4Z)-6-[(2α,3α)-2-(3-pyridyl)-3-pyrrolidinyl]-4-hexenoate 18.4 mmol of the compound prepared in stage D of Example 23 are stirred in 50 ml of trifluoroacetic acid at room temperature for ½ hour. The reaction medium is hydrolyzed with 250 ml of water and extracted with dichloromethane. The aqueous phase is alkalinized to pH 10 by adding 12N sodium hydroxide. The expected product is extracted with dichloromethane.

Yield 64%

| | Elemental microanalysis: | | |
|---|---|---|---|
| | C % | H % | N % |
| Calculated | 70.04 | 8.08 | 10.21 |
| Found | 69.46 | 8.05 | 10.07 |

STAGE B: Methyl (4Z)-6-[(2α,3α)-1-(4-chlorophenylaminocarbonyl)-2-(3-pyridyl)-3-pyrrolidinyl]-4-hexenoate A solution containing 6.2 mmol of 4-chlorophenyl isocyanate in 20 ml of tetrahydrofuran is added in small portions to a stirred solution at room temperature containing 6.2 mmol of the compound prepared in the preceding stage in 20 ml of tetrahydrofuran. Stirring is maintained for 48 hours. After concentration of the solvent, the expected product is purified by chromatography on silica gel, using a dichloromethane/methanol (95:5) mixture as eluent.

Yield: 57%

STAGE C:
(4Z)-6-[(2α,3α)-1-(4-Chlorophenylaminocarbonyl)-2-(3-pyridyl)-3-pyrrolidinyl]-4-hexenoic acid sodium salt This stage is identical to stage F of Example 21.
Yield: 73%

| Elemental microanalysis: | | | | |
|---|---|---|---|---|
| | C % | H % | N % | Cl % |
| Calculated | 60.62 | 5.32 | 9.64 | 8.13 |
| Found | 59.21 | 5.33 | 9.28 | 8.22 |

EXAMPLE 25

(4Z)-6-[(2α,3α)-1-(2-Hydroxybenzoyl)-2-(3-pyridyl)-3-pyrrolidinyl]-4-hexenoic acid sodium salt STAGE A: Methyl (4Z)-6-[(2α,3α)-1-(2-methoxybenzoyl)-2-(3-pyridyl)-3-pyrrolidinyl]-4-hexenoate A solution containing 6.6 mmol of o-methoxy- benzoyl chloride in 20 ml of toluene is added in small portions to a stirred solution at room temperature of 5.5 mmol of the compound prepared in stage A of Example 24 and 7.2 mmol of triethylamine in 50 ml of toluene. The reaction medium is stirred for 2 hours at room temperature and then treated with water. The expected product is obtained after drying and evaporation of the solvent.

Yield: 85%

Proton nuclear magnetic resonance (CDCl$_3$/TMS):
The coupling constant J between the two geminal protons 2α and 3α of the pyrrolidine is equal to 7 Hz.

STAGE B: Methyl (4Z)-6-[(2α,3α)-1-(2-hydroxybenzoyl)-2-(3-pyridyl)-3-pyrrolidinyl]-4-hexenoate The expected product is obtained from the compound described in the preceding stage using the process described in Example 14.

Yield: 35%
Melting point: 77° C.

STAGE C: (4Z)-6-[(2α,3α)-1-(2-Hydroxybenzoyl)-2-(3-pyridyl)-3-pyrrolidinyl]-4-hexenoic acid sodium salt Identical to stage F of Example 21.
Yield: 70%

| Elemental microanalysis: | | | |
|---|---|---|---|
| | C % | H % | N % |
| Calculated | 65.66 | 5.76 | 6.96 |
| Found | 64.78 | 5.40 | 6.90 |

EXAMPLE 26

(4Z)-6-{(2α,3α)-1-[(3-Pyridyl)methyl]-2-(3-hydroxyphenyl)-3-pyrrolidinyl}-4-hexenoic acid sodium salt STAGE A: (2α,3α)- 1-tert- Butoxycarbonyl-2-(3-methoxyphenyl)-3-(hydroxymethyl) pyrrolidine Prepared according to the process described in stage A of Example 23.
Yield: 60%
Proton nuclear magnetic resonance (CDCl$_3$/TMS):
The coupling constant J between the two geminal protons 2α and 3α of the pyrrolidine is equal to 9 Hz.

STAGE B to E

Stages B to D of this example are identical to stages C to E of Example 21; stage E is identical to stage A of Example 24.

STAGE F: Methyl (4Z)-6-{(2α,3α)-1-[(3-pyridyl)methyl]-2-(3-methoxyphenyl)-3-pyrrolidinyl}-4- hexenoate This product is prepared according to the same process as that described in stage A of Example 21, using the product prepared in the preceding stage as starting material.

Yield: 70%
Proton nuclear magnetic resonance (CDCl$_3$/TMS):
The coupling constant J between the two geminal protons 2α and 3α of the pyrrolidine is equal to 7 Hz.

STAGE G: Methyl (4Z)-6-{(2α,3α)-1-[(3-pyridyl)methyl]-2-(3-hydroxyphenyl)-3-pyrrolidinyl}-4-hexenoate Prepared according to the same process as that described in Example 14.
Yield: 99%

STAGE H: (4Z)-6-{(2α,3α)-1-[(3-Pyridyl)methyl]-2-(3-hydroxyphenyl)-3-pyrrolidinyl}-4-hexenoic acid sodium salt Prepared according to the same process as that described in stage F of Example 21.
Yield: 40%

| Elemental microanalysis: | | | |
|---|---|---|---|
| | C % | H % | N % |
| Calculated | 72.11 | 7.15 | 7.64 |
| Found | 71.53 | 7.14 | 7.92 |

PHARMACOLOGICAL STUDY OF THE COMPOUNDS OF THE INVENTION

EXAMPLE 27

Platelet aggregation

Rabbits (2-3 kg) are anesthetized with pentobarbital sodium (30 mg/kg i.v.). After cannulation of the left carotid artery, blood is withdrawn onto sodium citrate (0.109M) (1 vol. of citrate per 9 vol. of blood).

Platelet-rich plasma (PRP) is obtained by centrifugation (20° C.) at 250 g for 20 minutes, and platelet-poor plasma (PPP) by centrifugation at 1000 g (10 min). The number of platelets (PL) in the PRP is adjusted to 300-350,000 PL/mm$^3$ by dilution with autologous PPP. The PRP is stored at the temperature of the room until the time of the test, and is used within 4 hours following withdrawal.

Platelet aggregation is carried out at 37° C. in siliconed glass tubes using an aggregometer. The PRP and PL are stirred at 1000 rpm (revolutions per minute). In order to study the activity of thromboxane antagonists, the PRP is incubated for 1 min at 37° C., and the antagonist is then added for a period of 3 min before addition of the agonist U46619 (1.2 μM). The final volume in the cell is then 250 μl. The intensity of platelet aggregation is established by taking the maximum amplitude of the aggregation plots and is expressed as a percentage light transmission (% T). The activity of the antagonists is expressed as IC$_{50}$, that is to say the concentration of the substance which induces a 50% inhibition of the aggregation response induced by U46619.

In this test, the IC$_{50}$ values of the compounds of Examples 14 and 15 are equal to 2 10$^{-5}$M.

EXAMPLE 28

Determination of the $pA_2$ values on guinea pig trachea

Male albino guinea pigs weighing 400–500 grams were sacrificed by a blow to the back of the neck and by cervical elongation. The throat is opened and the trachea is rapidly removed and then cut into two-cartilage rings. These rings are mounted between two hooks in cells thermostated at 37° C. containing physiological fluid (composition in mM:NaCl 118; $NaHCO_3$ 25; glucose 10; KCl 4.7; $CaCl_2$ 1.25; $MgSO_4$ 1.19; $KH_2PO_4$ 1.14).

A 95% $O_2$/5% $CO_2$ mixture is bubbled through the physiological solution. The lower hook constitutes the fixed point while the upper hook is connected to an isometric strength gage. The tissues are placed under a baseline tension of 3.5 grams. The test pharmacological substances are prepared immediately before use. The drugs are solubilized in water or in dimethyl sulfoxide.

After mounting, the preparations are left standing for 90 minutes, rinses being performed every 30 minutes. After readjustment of the baseline tension, a contraction produced by a single dose of agonist (U46619; $10^{-5}$M) is produced in order to make the following contractions consist. After washing and return to the baseline, a first effect/concentration curve is established by adding cumulative doses of U46619 ($10^{-9}$M to $10^{-5}$M, with semi-log spacing between the doses). This first experiment enables the "control" 50% effective concentration ($EC_{50}$) to be calculated.

This $EC_{50}$ is routinely calculated in the following manner: the tension values are first converted to percentages relative to the maximum effect, these percentages then being plotted on a graph with the percentages as ordinates and the log (concentration) values as abscissae. A linear regression is then carried out on the points lying between 10% and 90% (which corresponds to the linear portion of the sigmoid curve). The concentration corresponding to half the maximum effect (50%) may be readily calculated using the parameters of the linear plot.

After washing and return to the baseline, the organ is brought into contact with the antagonist (8 different concentrations for each organ) for 20 minutes. A second effect/concentration curve is then established in the presence of the antagonist, and the "treated" $EC_{50}$ can then be calculated. All the elements enabling the $pA_2$ (competitive antagonism) or $pD_2$ (non-competitive antagonism) to be calculated are thereby obtained.

The $pA_2$ (which represents the negative logarithm of the antagonist concentration in the presence of which twice as much agonist is required in order to obtain the same effect) is determined by plotting on a graph the values of log ((L/1)−1) with respect to log (antagonist concentration), where L=effect in presence of antagonist and 1=control effect.

In this test, the $pA_2$ values of the compounds of Examples 1, 14 and 15 are as follows:
Example 1: $pA_2$=7.2
Example 21: $pA_2$=8.74
Example 14: $pA_2$=8
Example 22: $pA_2$=5.15
Example 15: $pA_2$=7.4
Example 26: $pA_2$=7.51

EXAMPLE 29

$IC_{50}$ on tracheal pressure in guinea pigs

Male albino guinea pigs (350–400 g) subjected to an 18-hour water diet are anesthetized with ethyl carbamate (1.25 g/kg i.p.). A catheter is introduced into the carotid artery in order to measure the arterial blood pressure by means of a pressure cell. A second catheter is introduced into the jugular vein and is used to inject the pharmacological substances. The trachea is cannulated and the guinea pig is placed in assisted respiration by means of a respirator. The animal's temperature is maintained at 37° C. using a thermostated blanket. A needle pushed into the tracheal cannula is connected to a pressure cell and enables the tracheal pressure to be recorded.

The guinea pigs are pretreated with d-tubocurarine (1 mg/kg i.v.) and with indomethacin (10 mg/kg i.v.). Injected at a dose of 2 µg/kg i.v., U46619 produces a bronchoconstriction which leads to an increase in tracheal pressure and induces an increase in arterial blood pressure. The responses to U46619 are reversible and reproducible if the injections are carried out every 10 minutes.

The thromboxane receptor antagonists are injected 5 minutes before the injections of U46619. The dose of antagonist that inhibits by 50% the increase in tracheal pressure caused by U46619 is determined ($IC_{50}$).
Example 4: $IC_{50}$=0.7 mg/kg
Example 14: $IC_{50}$=0.07 mg/kg
Example 15: $IC_{50}$=0.16 mg/kg
Example 21: $IC_{50}$=0.17 mg/kg
Example 26: $IC_{50}$=0.03 mg/kg

EXAMPLE 30

Anti-thromboxane synthase activity

Albino New Zealand rabbits weighing approximately 2 kg are used. These rabbits are anesthetized with pentobarbital (30 mg/kg i.v.). Blood is collected via carotid catheter in dry glass tubes, in the proportion of 1 ml per tube, in the presence or absence of different concentrations of inhibitor. The inhibitors are diluted in physiological fluid in order to avoid possible hemolysis.

The tubes are placed in a water bath at 37° C. for one hour. After coagulation, the tubes are cooled to 4° C. and centrifuged at 2000 g for 20 minutes in order to separate the serum from the clot. The serum may be frozen at −20° C. for 2 weeks for a subsequent assay.

The levels of $TXB_2$, the stable metabolite of $TXA_2$, in the serum are determined by radio immunoassay.

The levels obtained in the presence of the different doses of inhibitor are converted to a percentage inhibition relative to the baseline level of $TXB_2$, in order to calculate the $IC_{50}$ of the inhibitor. The latter is obtained by non-linear regression using the following equation (Michaelis L, Menten ML, Die Kinetik der Invertinwirkung, Biochem. Zeitschrifft, 1913, 49, 333-369):

$$I = (Imax * C^n) / (IC^n + C^n)$$

where
I=inhibition
Imax=maximum inhibition
C=inhibitor concentration
IC=$IC_{50}$
n=Hill coefficient
Example 2: $IC_{50}$=$2 \times 10^{-4}$M Example 20: $IC_{50} = 6 \times 10^{-5} M$
Example 21: $IC_{50} = 8.5 \times 10^{-6} M$

EXAMPLE 31

Pharmaceutical composition

Preparation formula for 1000 tablets containing a 10 mg dose

| Compound of Example 1 | 10 g |
|---|---|
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

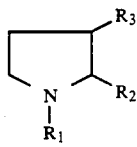

in which:

$R_1$ represents:
linear or branched ($C_1-C_6$) alkyl, unsubstituted or substituted with 2-pyridyl, 3-pyridyl, or phenyl (itself optionally substituted with one or more halogen or linear or branched ($C_1-C_6$) alkyl, linear or branched ($C_1-C_6$) alkoxy or trihalomethyl), phenyl, unsubstituted or substituted with one or more hydrogen or linear or branched ($C_1-C_6$) alkyl, linear or branched ($C_1-C_6$) alkoxy or trihalomethyl, pyridyl, phenylsulfonyl, unsubstituted or substituted on the phenyl ring with one or more halogen or linear or branched ($C_1-C_6$) alkyl, linear or branched ($C_1-C_6$) alkoxy or trihalomethyl, linear or branched

linear or branched

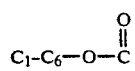

benzoyl (unsubstituted or substituted on the phenyl ring with one or more halogen, hydroxyl, $C_1-C_6$ alkyl, $C_1-C_6$ alkoxy, or trifluoromethyl) or pyridylcarbonyl, $C_1-C_6$ alkylaminocarbonyl or phenylaminocarbonyl (unsubstituted or substituted on the phenyl ring with one or more halogen, hydroxyl, $C_1-C_6$ alkyl, $C_1-C_6$ alkoxy, or trifluoromethyl),

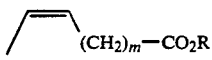 or 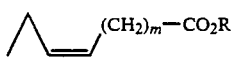

$R_2$ represents:
phenyl, unsubstituted or substituted with one or more halogen or linear or branched ($C_1-C_6$) alkyl, linear or branched ($C_1-C_6$) alkoxy, hydroxyl or trihalomethyl,
3-pyridyl or 2-pyridyl, $R_3$ represents any one of the following groups:

/⎯\(CH$_2$)$_m$—CO$_2$R

/⎯\(CH$_2$)$_m$—CO$_2$R

—(CH$_2$)$_n$—CO$_2$R in which
m is equal to 2, 3 or 4,
n is equal to 4, 5, 6, or 7,
and R represents hydrogen or a linear or branched ($C_1-C_6$) alkyl, its enantiomers, diastereoisomers and epimers, as well as its addition salts with a pharmaceutically-acceptable acid or base.

2. A compound of claim 1 selected from those in which $R_1$ represents substituted or unsubstituted phenylsulfonyl, its enantiomers, diastereoisomers and epimers, as well as its addition salts with a pharmaceutically-acceptable acid or base.

3. A compound of claim 1 selected from those in which $R_1$ represents 3-pyridylmethyl, its enantiomers, diastereoisomers and epimers, as well as its addition salts with a pharmaceutically-acceptable acid or base.

4. A compound of claim 1 selected from those in which $R_2$ represents substituted or unsubstituted phenyl, its enantiomers, diastereoisomers and epimers as well as its addition salts with a pharmaceutically-acceptable acid or base.

5. The compound of claim 1, selected from (4Z)-6-{(2α,3α)-1-[(3-pyridyl)methyl]-2-phenyl-3-pyrrolidinyl}-4-hexenoic acid, its enantiomers and diastereoisomers, as well as its addition salts with a pharmaceutically-acceptable base or acid.

6. A method for treating an animal or human living body afflicted with a thrombotic cardiovascular disease or an airway disease requiring a thromboxane $A_2$ receptor antagonist or thromboxane $A_2$ synthase inhibitor comprising the step of administering to the living body an amount of a compound of claim 1 which is effective for alleviation of said condition.

7. A pharmaceutical composition comprising as active principle an effective thromboxane $A_2$ receptor antagonistic or thromboxane $A_2$ synthase inhibitory amount of a compound of claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,296,494
DATED : Mar. 22, 1994
INVENTOR(S) : Gilbert Lavielle, Patrick Hautefaye, Michel Laubie, Tony Verbeuren It is certified that error appears in the above-indentified patent and that said Letters Patent is hereby corrected as shown below:

Title Page, Column 1, [30] under Foreign Application Priority
    Date; "Dec. 30, 1991" should read -- Dec. 20, 1991 --.
Column 14, line 3; "((2α," should read --{(2α, --.
Column 14, line 4; "-pyrrolidinyl]" should read
    -- -pyrrolidinyl} --.
Column 22, approximately line 41; "epimers as"
    should read -- epimers, as --.

Signed and Sealed this

Sixth Day of September, 1994

Attest:

BRUCE LEHMAN

*Attesting Officer*     *Commissioner of Patents and Trademarks*